United States Patent [19]
Jensen

[11] Patent Number: 5,501,677
[45] Date of Patent: Mar. 26, 1996

[54] TWO-PIECE OSTOMY APPLIANCE AND LOW-PROFILE COUPLING RING ASSEMBLY

[76] Inventor: Ole R. Jensen, 646 Orangeburgh Rd., River Vale, N.J. 07675

[21] Appl. No.: 262,599

[22] Filed: Jun. 20, 1994

[30] Foreign Application Priority Data

Jun. 25, 1993 [DK] Denmark ................... 759/93

[51] Int. Cl.⁶ ................................................. A61F 5/44
[52] U.S. Cl. ............................................. 604/338; 604/332
[58] Field of Search ................................ 604/332–338

[56] References Cited

U.S. PATENT DOCUMENTS

| | | | |
|---|---|---|---|
| 3,528,420 | 9/1970 | Nielsen | 128/283 |
| 4,078,567 | 3/1978 | Fenton . | |
| 4,359,051 | 11/1982 | Oczkowski | 128/283 |
| 4,419,100 | 12/1983 | Alexander | 604/339 |
| 4,460,363 | 7/1984 | Steer et al. | 604/336 |
| 4,518,389 | 5/1985 | Steer et al. | 604/339 |
| 4,610,676 | 9/1986 | Schneider et al. | 604/339 |
| 4,610,677 | 9/1986 | Mohiuddin | 604/339 |
| 4,786,285 | 11/1988 | Jambor | 604/342 |
| 4,808,173 | 2/1989 | Kay | 604/339 |
| 4,828,553 | 5/1989 | Nielsen | 604/339 |
| 4,846,820 | 7/1989 | Jensen | 604/339 |
| 4,931,045 | 6/1990 | Steer | 604/338 |
| 4,950,261 | 8/1990 | Steer | 604/339 |
| 5,167,651 | 12/1992 | Leise, Jr. et al. | 604/339 |
| 5,257,981 | 11/1993 | Takahashi | 604/332 |
| 5,429,625 | 9/1995 | Holmberg | 604/338 |

FOREIGN PATENT DOCUMENTS

| | | |
|---|---|---|
| 0089138 | 4/1988 | European Pat. Off. . |
| 0142259 | 8/1988 | European Pat. Off. . |
| 0429199 | 5/1991 | European Pat. Off. . |
| 1217406 | 12/1970 | United Kingdom . |
| 1274382 | 5/1972 | United Kingdom . |
| 1571657 | 7/1980 | United Kingdom . |
| 1583027 | 1/1981 | United Kingdom . |
| 1586824 | 3/1981 | United Kingdom . |
| 1586823 | 3/1981 | United Kingdom . |
| 2147810 | 5/1985 | United Kingdom . |
| 2151482 | 7/1985 | United Kingdom . |
| 2173403 | 10/1986 | United Kingdom . |
| 2153683 | 12/1987 | United Kingdom . |
| 2190841 | 3/1988 | United Kingdom . |
| WO85/03427 | 8/1985 | WIPO . |
| WO91/01118 | 2/1991 | WIPO . |
| WO91/18566 | 12/1991 | WIPO . |

*Primary Examiner*—Randall L. Green
*Assistant Examiner*—Mark O. Polutta
*Attorney, Agent, or Firm*—Tilton Fallon Lungmus

[57] ABSTRACT

A two-piece ostomy appliance, and a low-profile coupling ring assembly therefor, in which the rings have relatively large flat flanges that extend in close proximity when the rings are coupled and in which the assembly has a radial/axial aspect ratio, with the radial dimension being measured outwardly from the stoma-receiving opening of the assembly, of at least 1.5 to 1, and preferably at least 2.5 to 1. One ring has an integral collar with an external latching shoulder and an annular sealing surface extending outwardly from the shoulder and merging with one of the side surfaces of the flange of that ring. The other ring includes a tapered, flexible, axially extending sealing lip that faces towards the first ring and is sealingly engagable with the sealing surface of the first ring when the rings are coupled together. The second ring also has a radially inwardly extending latching rib engagable with the shoulder of the first ring for retaining the rings in coupled condition, the latching rib being of smaller inside diameter than the annular sealing lip.

17 Claims, 1 Drawing Sheet

TWO-PIECE OSTOMY APPLIANCE AND LOW-PROFILE COUPLING RING ASSEMBLY

BACKGROUND

Ostomy appliances of the so-called "two-piece" type are well known and consist essentially of an adhesive faceplate for adhesive attachment to the peristomal skin surfaces of a patient and a collection pouch that is detachably connectable to the faceplate. The faceplate and pouch have alignable stoma-receiving openings, and a pair of thermoplastic coupling rings are secured to the faceplate and pouch about such openings for connecting the parts together. The advantage of such a two-piece appliance over a conventional one-piece appliance (in which a pouch and faceplate are permanently connected) is that a number of pouches may be used successively with a single faceplate. The user of a two-piece appliance may therefore leave a faceplate adhesively attached to the skin for an extended period, without the discomfort, inconvenience, and skin irritation that frequent removal and replacement of an adhesive faceplate may involve, and simply remove a used pouch and replace it with a fresh pouch whenever needed.

To be effective, however, it is critical that a two-piece appliance be free of leakage problems since even slight leakage of liquid, solid, or gaseous matter could cause considerable inconvenience and embarrassment to the wearer. Much effort has been expended in the past to develop coupling systems that are reliable and not likely to be inadvertently detached in use, are nevertheless easy to assemble and disconnect at will, and do not leak even when a number of pouch rings have been successively coupled and uncoupled from a single faceplate ring. While some existing appliances come closer than others to fully achieving these objectives, their effectiveness in doing so has generally come at the sacrifice of one further objective—that of providing a coupling assembly of low enough profile that it does not protrude an appreciable distance from a wearer's body and does not produce conspicuous bulges through a wearer's clothing.

For example, some two-piece appliances utilize a coupling system in which one of the rings is channel-shaped (in radial cross section) and the mating ring includes an annular rib that is receivable in the channel to make both sealing and latching contact with the channel's inner surfaces. Reference may be had to patents U.S. Pat. No. 4,419,100, GB 1,571,657, GB 1,583,027 and EP 0 089 138 for couplings of the channel-and-rib type. While such constructions may provide latching and sealing effectiveness, they are all of relatively high profile and fail to lie flat against a patient's body. A further disadvantage is that in some channel-and-rib couplings, liquid-tight (and gas-tight) sealing is achieved by means of a thin-deflectable sealing lip extending from the rib of the faceplate ring, with such sealing lip often contributing to a latching function. After a number of coupling and uncoupling procedures, wear and damage of the faceplate ring often occurs so that the deflectable lip is no longer capable of performing an effective sealing function. Usually such wear or damage goes unnoticed until leakage results.

Patent U.S. Pat. No. 3,528,420 also discloses a coupling in which the sealing and latching functions are performed in the same contact areas. Attachment security may be compromised and the sealing surfaces easily worn or damaged by successive attachment and removal of pouches. U.S. Pat. No. 4,610,676 and U.S. Pat. No. 4,610,677 disclose coupling systems in which the latching zones are located radially outboard from the sealing zones; however, the sealing surfaces nevertheless must make repeated and forceful contact, with the risk of possible wear and damage, when pouches are successively attached to and removed from the reusable faceplates.

Other references indicating the state of the art are U.S. Pat. Nos. 4,786,285, 4,828,553, 4,460,363, 4,808,173, 4,846,820, 4,359,051, 4,518,389, and 4,950,261; GB patents and published applications 1,586,823, 2,153,683, 1,586,824, 1,217,406, 2,190,841, 1,274,382, 2,147,810A, 2,173,403A, and 2,151,482A; International publications WO 91/01118 and WO 85/03427; and European patents and application 0 089 138, 0 142 259, and 0 429 199A.

SUMMARY OF THE INVENTION

One aspect of this invention lies in recognizing that while security of attachment and sealing effectiveness of the plastic coupling rings of a two-piece appliance depend in part on providing such rings with sufficient stiffness, it is possible to attain that stiffness by extending the rings radially rather than axially as in the past. The coupling rings of this invention may be larger in radial dimensions than the rings of currently-available coupling systems, but their axial dimensions, especially when coupled together, are substantially less. The result is a coupling assembly that is relatively flat or of low profile. More precisely, when arcuate segments of the rings (when coupled together) are viewed in radial section, they have a relatively high aspect ratio—that is, the ratio of their radial dimension to their axial dimension is substantially greater than 1.5 to 1 and preferably greater than 2.5 to 1.

Each of the rings has a relatively large and flat annular flange, with the flanges of the two rings being of substantially the same size measured radially from the openings of the rings. When such rings are latched together, their flanges extend outwardly in close proximity with the tapered flange of the pouch ring being near the adhesive patch that secures the faceplate (and the assembly as a whole) to a wearer's skin. One of the rings (the male ring) is provided with an annular collar having an external latching shoulder. The other ring (the female ring) receives the collar when the rings are coupled together, with the female ring having an inwardly-extending rib engaging the external shoulder and latching the two rings together. When the rings are so coupled, the axial dimension of the assembly does not exceed the axial collar dimension of the male ring alone, such dimension being less than 5 mm and preferably less than 4 mm.

A fluid-tight seal between the parts is achieved by means of a tapered, flexible, annular sealing lip that extends axially from the female ring and yieldably engages a smooth annular sealing surface of the male ring. Of particular importance is the fact that the annular sealing lip in its unflexed state has an inside diameter larger than the outside diameter of the latching shoulder of the other ring. Consequently, the two rings may be coupled and uncoupled without bringing the sealing lip of the female ring (preferably used as the pouch ring) into deforming and possibly damaging engagement with the latching shoulder of the male ring (preferably used as the faceplate ring).

Because of their relatively high aspect ratios and limited axial dimensions, the rings are not only of relatively low profile but are also easily manipulated when attachment or detachment is desired. The wide flanges and their close juxtaposition when the rings are coupled make it easy for a user to apply the force needed to unlatch the rings. The flanges function as radially-extending lever arms to facilitate unlatching and separation of the rings, and their large size also aids a user in aligning and joining the rings.

Other features, advantages, and objects will appear from the specification and drawings.

DRAWINGS

DETAILED DESCRIPTION OF PREFERRED EMBODIMENT

Figure 1:
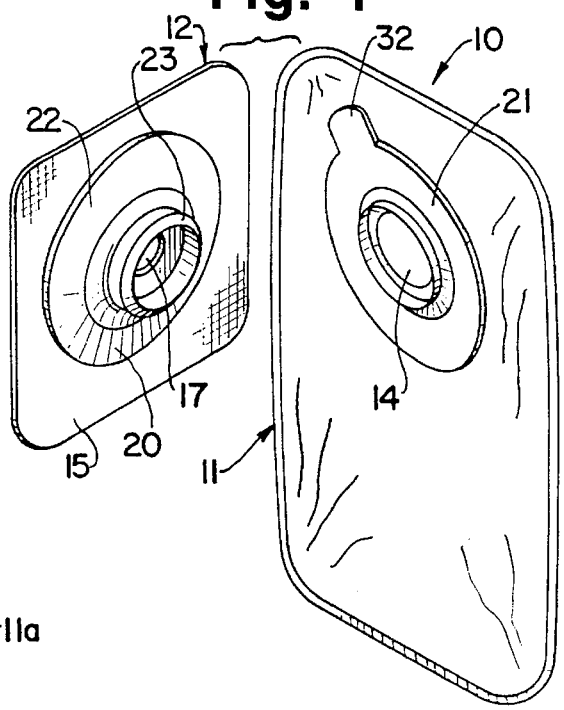
FIG. 1 is a perspective view of an ostomy appliance embodying this invention, the two pieces of the appliance being shown in separated condition for clarity of illustration.

In the embodiment illustrated in the drawings, the numeral 10 generally designates a two-piece ostomy appliance consisting essentially of a pouch component 11 and a faceplate component 12. Except for their coupling rings, the two components are conventional. The pouch has walls 11a and 11b joined together along their outer margins by any suitable means, as by heat seal 13, and one of the walls 11b is provided with a stoma-receiving opening 14.

The faceplate component 12 includes a flexible patch 15 with a bodyside surface coated with pressure sensitive adhesive 16. Like wall 11b of the pouch, the patch 15 has a stoma-receiving opening 17 that registers with pouch opening 14 when the components are assembled. Faceplate opening 17 is shown to be relatively small in FIG. 1, but it is to be understood that such opening is a starter opening that would be enlarged by the user (or healthcare provider) at the time of application so that the final opening in the faceplate would closely match the size and shape of the patient's stoma.

Patch 15 may be formed of any soft conformable material such as the microporous non-woven sheet materials now commonly used in ostomy appliances. Such materials are considered desirable because of their porosity and breathability, but other materials that are non-porous, particularly materials having moisture vapor transmission rates approaching that of skin, may also be used. For example, polyurethane films have been effectively used for such purposes, and other polymeric films and polymeric foam materials may also be used. The adhesive coating 16 for the patch may be any medical-grade pressure-sensitive adhesive, such as an acrylic adhesive. Alternatively, the adhesive may take the form of any of a variety of known hydrocolloid-containing skin barrier materials that not only have dry and wet tack but are also capable of absorbing moisture from the skin. Since all of such materials and the procedures for applying them are well known and do not constitute features of the present invention, except for the coupling rings with which they are associated, further discussion of such materials and procedures is believed unnecessary herein.

The coupling ring assembly comprises a first coupling ring 20 and a second coupling ring 21, both formed of flexible thermoplastic material. Low-density polyethylene is believed particularly suitable, but other polymeric materials having similar properties of flexibility and toughness may be used. In the embodiment illustrated, ring 20 is shown as the faceplate ring and ring 21 as the pouch ring and, while that is considered the preferred orientation for reasons indicated below, it is believed possible to construct an assembly in which the first ring (the male ring) is instead affixed to the pouch and the second ring (the female ring) to the faceplate.

The first ring 20 includes a flat annular flange 22 and an integral annular collar 23, the latter defining a stoma-receiving opening 24 extending through the ring. Flange 22 is of substantial radial extent and has generally planar side surfaces, namely, bodyside surface 22a and pouchside surface 22b. The bodyside surface is secured by heat seal 25 or by any other suitable means to patch 15. While the entire surface 22a may be so attached to the patch, it is believed preferably to secure the two together only along the innermost portion of the flange (as shown) so that a user may insert his/her fingers between the outer portion of the flange and the patch during a coupling operation. Leaving the outer portion of the flange unattached to the patch also allows the flexible and deformable patch to conform more closely with the changeable contours of the body wall to which the patch is adhesively attached, without constraints that would otherwise be provided by the relatively stiff flange 22 if that flange were joined along its full radial extent to the patch.

Figure 2:
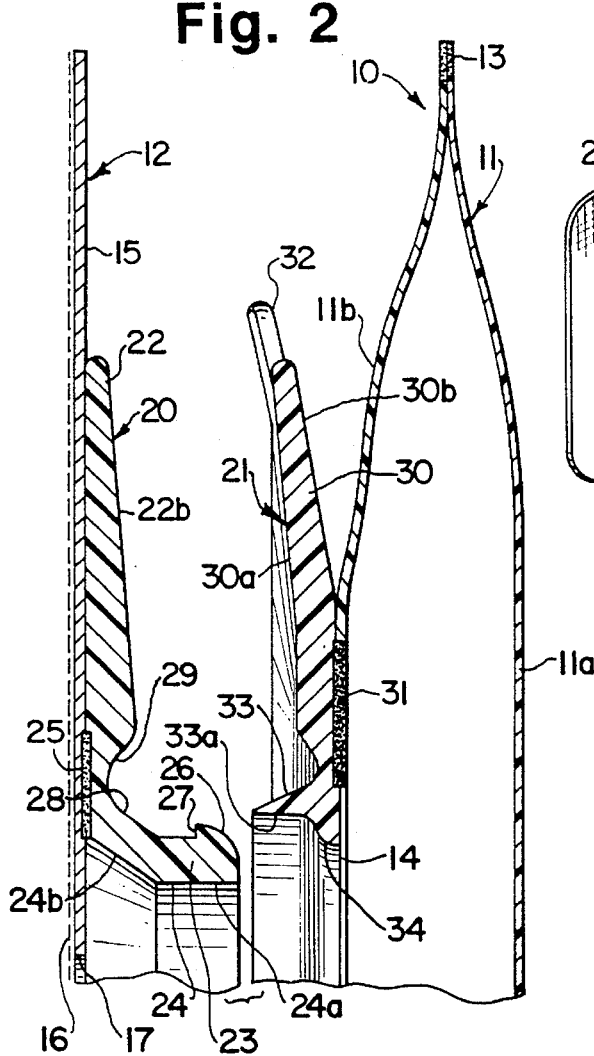
FIG. 2 is an enlarged, fragmentary vertical sectional view of the components in separated condition.

The collar 23 extends axially from the flange and is provided with an enlarged, rounded end portion 26 defining an external annular shoulder 27. A sealing surface 28 extends in a bodyside direction from that shoulder and slopes radially outwardly to merge smoothly with pouchside surface 22b of the flange. Ideally, a smoothly-curved annular depression or recess 29 serves as an extension of the sealing surface 28 and contributes to a highly effective seal between the two rings when they are coupled together as described below. Referring to FIG. 2, it will be observed that the inner surface 24 of the collar 23, which defines the stoma-receiving opening of coupling ring 20, includes a generally cylindrical distal portion 24a and a frusto-conical proximal portion 24b.

The second ring 21, which is the pouch ring in the illustrated embodiment, also has a flat annular flange 30 of substantial radial extent. Most advantageously, flange 30 is of approximately the same size as flange 22 of the faceplate ring. While referred to as flat, the flange 30 may be slightly dish-shaped as shown with its concave or bodyside surface 30a facing towards the faceplate coupling ring 20 when the two rings are aligned for attachment as depicted in FIG. 2.

The pouchside surface 30b has its inner portion secured by heat seal 31 or by any other suitable means to the wall 11b of pouch 11 about the stoma-receiving opening 14 of that pouch. Since the outer portion of surface 30b is unsecured to the pouch wall, a user may easily insert his/her fingers between ring 21 and the pouch during attachment and detachment procedures. The outer margin of the flange 30 may be provided with an integral tab or tongue 32 which projects radially outwardly beyond the periphery of faceplate ring 20 when the two rings are coupled together. By gripping tab 32, a user may easily initiate the application of force for separating the two rings and thereby detaching pouch 11 from faceplate 12.

Figure 4:
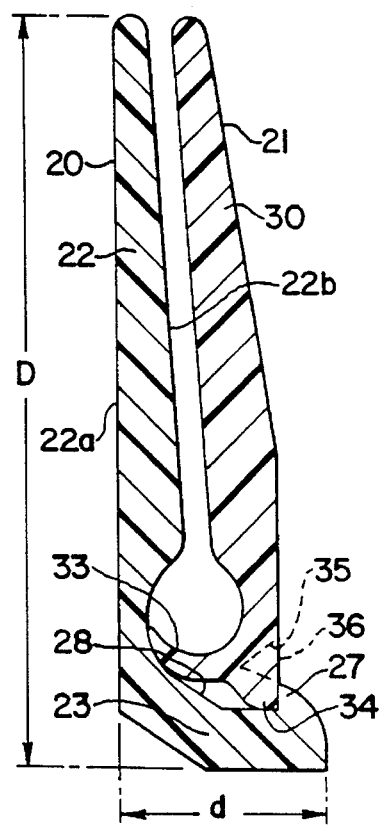
FIG. 4 is a further enlarged sectional view showing the relationship of the rings in fully coupled condition.

The pouch ring 21 also includes a tapered, flexible, axially-extending sealing lip 33. The annular sealing lip is formed integrally with flange 21 and faces towards the other coupling ring when the parts are assembled or aligned for assembly as depicted in FIGS. 4 and 2, respectively. The tapered lip is dimensioned to engage sealing surface 28 when the rings are coupled together. It will be noted that the inside diameter of the annular lip is substantially larger than the outside diameter of collar end portion 26 and shoulder 27. It will also be noted that the inner surface 33a of the lip is of substantially uniform diameter (i.e., cylindrical) so that the tapered lip may be easily slipped over the end of the collar without forcefully bearing against the collar surfaces adjacent shoulder 27.

Coupling ring 21 also includes an annular latching rib 34 that extends radially inwardly from the base of lip 33 and is dimensioned to engage shoulder 27 for latching the rings together when they are fully assembled as depicted in FIG. 4. Under such conditions, the sealing lip 33 is cammed outwardly by the sealing surface 28 and, particularly because of its stretched and tensioned (hoop-stressed) condition, maintains fluid-tight (both gas- and liquid-tight) sealing contact with the faceplate ring.

Figure 3:
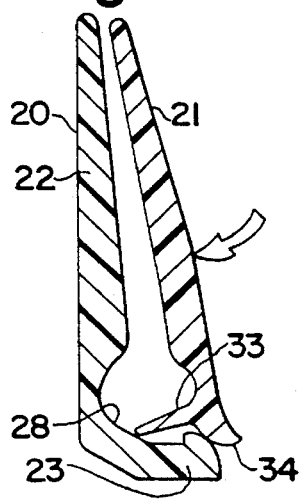
FIG. 3 is a simplified sectional view illustrating the relationship of the coupling rings at the commencement of a coupling operation.

FIG. 3 schematically depicts the coupling rings during an initial stage of assembly. The sealing lip 33 has cleared the shoulder of collar 23 without encountering resistance or deformation but, as the latching rib 34 engages the end of the collar and the forces urging rings together are continued, the sealing lip 33 is brought into contact with sealing surface 28. Continued application of force causes outward deformation or stretching of the sealing lip 33 as shown in FIG. 4, with such deformation continuing until latching rib 34 clears the end of collar 23 and engages shoulder 27.

Figure 5:
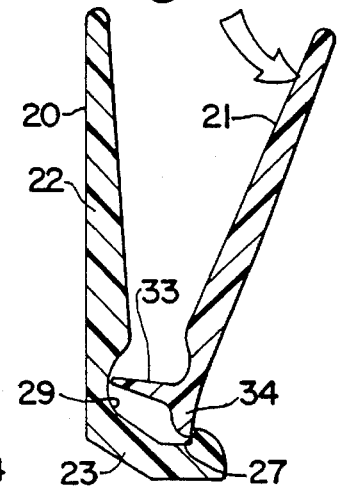
FIG. 5 is a sectional view similar to FIG. 3 but showing the relationship of parts at the commencement of an uncoupling operation.

Separation of the rings is initiated by gripping the flange 30 of ring 21 and pulling its outer portion away from the flange 22 of faceplate ring 20. A lever action occurs with the flange of ring 21 pivoting outwardly about the point of contact between latching rib 34 and shoulder 27 (FIG. 5). The sealing lip 33 sweeps outwardly within annular recess 29 until it no longer contacts the sealing surface of coupling ring 20 and the latching rib 34 finally disengages from shoulder 27.

While the positions of coupling rings 20 and 21 might be interchanged, with the female ring 21 attached to faceplate patch 15 and the male ring 20 affixed to pouch 11, the arrangement shown in the drawings is preferred because, among other things, the collar 23 of ring 20 defines the innermost limits of the coupling ring assembly. Since ring 21 is of larger inside diameter, it may be easily attached and removed without risking direct contact with the patient's stoma and the sensitive peristomal skin surfaces. Also, when the parts are arranged as shown, the end portion 26 of the collar is located within pouch 11 when the parts are fully assembled, thereby effecting a further reduction in the profile of the assembly.

The profile of the assembly is essentially controlled by the dimensions of the first ring or male ring 20, as shown most clearly in FIG. 4. Dimension D, which is the maximum cross-sectional dimension of the two-ring assembly measured radially outwardly from opening 24a (excluding only an optional tab portion 32 which may project outwardly beyond the border of flange 22), is the dimension of the first ring itself. Similarly, the axial dimension d of the assembly is the length of collar 23 of the first ring. The parts therefore nest together almost entirely within the radial and axial dimensions of the first or faceplate ring 20, with the flanges 22 and 30 of the two rings extending outwardly in close proximity as shown in FIG. 4.

Despite the low profile of the assembly, secure latching and sealing engagement is achieved in part because of the strength and stiffness resulting from the substantial radial dimensions of such rings. The axial dimension d of the assembly, which is responsible for the relatively flat or low profile of that assembly, should be less than 5 mm and preferably less than 4 mm. Effective results are obtainable from an assembly of the general configuration depicted in the drawings in which dimension d is approximately 3.5 mm. To achieve sealing and latching effectiveness with an assembly having such low profile, the aspect ratio (D/d) should be greater than 1.5 to 1 and preferably greater than 2.5 to 1. Particularly effective results may be obtained where such ratio is approximately 3.3 to 1.

In the illustrated embodiment, coupling ring 21 is shown to be formed as a unitary or one-piece structure of flexible thermoplastic material. However, to facilitate latching/unlatching action and, in particular, the action of rib 34 as it deforms slightly to clear shoulder 27, the pouchside surface of the ring just outboard (radially outwardly) of the rib may be provided with an annular channel or groove 35 preferably filled with an insert 36 of natural or synthetic rubber or other readily deformable elastomeric material (FIG. 4).

While in the foregoing, I have disclosed an embodiment of the invention in considerable detail for purposes of illustration, it will be understood by those skilled in the art that many of these details may be varied without departing from the spirit and scope of the invention.

I claim:

1. A low-profile coupling ring assembly for a two-piece ostomy appliance, comprising first and second coupling rings formed of flexible thermoplastic material and defining alignable stoma-receiving openings; said first ring having a flat annular flange with generally planar side surfaces and having an integral collar extending from said flange immediately adjacent to and about the stoma-receiving opening of said first ring; said collar having an external annular latching shoulder and having an annular sealing surface extending outwardly from said shoulder and merging with one of said side surfaces; said second ring also having a flat annular flange with generally planar side surfaces and having a tapered, flexible, axially-extending annular sealing lip facing towards said first ring and engagable with said sealing surface when said rings are coupled together; said second ring also having a radially inwardly extending annular latching rib engagable with said shoulder for retaining said rings in coupled condition; said rings when coupled together having an overall radial/axial dimensional aspect ratio measured outwardly and axially from said stoma-receiving opening of said first ring of at least 1.5 to 1.

2. The assembly of claim 1 in which said flanges of said first and second coupling rings are of substantially the same outside diameter.

3. The assembly of claims 1 or 2 in which said flanges of said first and second rings are disposed in close proximity when said rings are coupled together.

4. The assembly of claim 3 in which said side surfaces of said flanges that face in opposite directions each from the other of said rings are spaced apart a distance substantially less than the axial dimension of said collar when said rings are coupled together.

5. The assembly of claim 1 in which said aspect ratio is at least 2.5 to 1.

6. The assembly of claims 1 or 5 in which said collar has an axial dimension less than 5 mm.

7. The assembly of claim 6 in which said collar has an axial dimension less than 4 mm.

8. The assembly of claim 6 in which said sealing lip has an inside diameter greater than the outside diameter of said shoulder.

9. A two-piece ostomy appliance for peristomal attachment to a patient's body, comprising a pouch component and an adhesive faceplate component provided with alignable stoma-receiving openings and including a pair of flexible, thermoplastic, faceplate and pouch coupling rings for detachably and sealingly coupling said components together; said faceplate coupling ring having a flat annular flange with generally planar pouchside and bodyside surfaces and having an integral collar extending away from said flange in a pouchside direction immediately about the stoma-receiving opening of said faceplate; said collar having an external annular latching shoulder at its pouchside end and having an annular external sealing surface sloping radially outwardly from said shoulder to the pouchside surface of said flange; said pouch coupling ring also having a flat annular flange with generally planar pouchside and bodyside surfaces and having an integral, flexible, annular sealing lip extending about the stoma-receiving opening of said pouch in a bodyside direction towards said faceplate and into forceful sealing engagement with said sealing surface when said rings are coupled together; said pouch coupling ring also having a radially inwardly extending annular latching rib engagable with said shoulder for holding said rings in latched condition.

10. The appliance of claim 9 in which said rings when coupled together having an overall radial/axial dimensional aspect ratio, measured radially outwardly and axially from said stoma-receiving opening of said faceplate ring, of at least 1.5 to 1.

11. The appliance of claim 10 in which said aspect ratio is at least 2.5 to 1.

12. The appliance of claim 10 in which said collar has an axial dimension less than 5 mm.

13. The appliance of claim 12 in which said collar has an axial dimension less than about 4 mm.

14. The appliance of claims 9 or 10 in which said flanges of said faceplate and pouch coupling rings are of substantially the same outside diameter.

15. The appliance of claim 14 in which said flanges of said pouch and faceplate coupling rings are disposed in close proximity when said rings are coupled together.

16. The appliance of claim 9 in which said sealing lip has an inside diameter greater than the outside diameter of said shoulder.

17. The appliance of claim 9 in which said pouch coupling ring is provided with an annular channel along the pouchside surface thereof adjacent said annular latching rib; and an insert of elastomeric material secured in said channel.

* * * * *